United States Patent
Arora et al.

(10) Patent No.: US 11,389,390 B2
(45) Date of Patent: Jul. 19, 2022

(54) COMPOSITIONS CONTAINING POLYMERS, WAX, AND CATIONIC SURFACTANT FOR CONDITIONING AND STYLING HAIR

(71) Applicant: L'OREAL, Paris (FR)

(72) Inventors: Shilpa Arora, South Plainfield, NJ (US); Marie Huynh, Monmouth Junction, NJ (US); Lisa Chuyin Ye-Tse, Brooklyn, NY (US); Bayle Augustin, Union, NJ (US); Aziza Khader Suleiman, Paterson, NJ (US); Anand Ramchandra Mahadeshwar, Mumbai (IN)

(73) Assignee: L'OREAL, Paris (FR)

( * ) Notice: Subject to any disclaimer, the term of this patent is extended or adjusted under 35 U.S.C. 154(b) by 179 days.

(21) Appl. No.: 16/428,872

(22) Filed: May 31, 2019

(65) Prior Publication Data

US 2020/0375876 A1    Dec. 3, 2020

(51) Int. Cl.
*A61K 8/898* (2006.01)
*A61K 8/92* (2006.01)
*A61Q 5/06* (2006.01)
*A61K 8/73* (2006.01)

(52) U.S. Cl.
CPC .............. *A61K 8/898* (2013.01); *A61K 8/73* (2013.01); *A61K 8/922* (2013.01); *A61K 8/927* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 3,110,695 A | 11/1963 | Ceresa | |
| 3,304,273 A | 2/1967 | Stamberger | |
| 3,383,351 A | 5/1968 | Stamberger | |
| 3,412,054 A | 11/1968 | Milligan et al. | |
| 3,523,095 A | 8/1970 | Laurito et al. | |
| 5,523,079 A | 6/1996 | Gough | |
| 5,658,558 A | 8/1997 | Schwartz | |
| 6,156,298 A | 12/2000 | Karlen et al. | |
| 6,358,502 B1 | 3/2002 | Tanabe et al. | |
| 7,226,582 B2 | 6/2007 | Traynor et al. | |
| 8,287,844 B2 | 10/2012 | Burgo | |
| 9,072,686 B2 | 7/2015 | Bui et al. | |
| 9,295,632 B1 | 3/2016 | Benn et al. | |
| 9,801,808 B2 | 10/2017 | Tan et al. | |
| 2005/0025736 A1 | 2/2005 | Jachowicz et al. | |
| 2007/0154402 A1 | 7/2007 | Trumbore et al. | |
| 2007/0197729 A1 | 8/2007 | Wolff et al. | |
| 2009/0060858 A1 | 3/2009 | Schwarzwaelder et al. | |
| 2009/0136439 A1 | 5/2009 | Feng et al. | |
| 2010/0008885 A1 | 1/2010 | Daly et al. | |
| 2011/0120487 A1 | 5/2011 | Rollat-Corvol et al. | |
| 2011/0150807 A1 | 6/2011 | Bui et al. | |
| 2011/0318286 A1 | 12/2011 | Kawasaki et al. | |
| 2013/0142748 A1* | 6/2013 | Tamura | A61Q 5/02 424/70.12 |
| 2013/0302267 A1 | 11/2013 | Peffly et al. | |
| 2014/0342968 A1 | 11/2014 | Hourigan et al. | |
| 2015/0004117 A1 | 1/2015 | Tan et al. | |
| 2015/0004119 A1 | 1/2015 | Tan et al. | |
| 2015/0079015 A1 | 3/2015 | Bolognini et al. | |
| 2016/0175238 A1 | 6/2016 | Shin et al. | |
| 2018/0092826 A1 | 4/2018 | Comeron et al. | |
| 2018/0311139 A1 | 11/2018 | Perner et al. | |
| 2020/0170911 A1* | 6/2020 | Dussaud | A61Q 5/04 |
| 2020/0206121 A1 | 7/2020 | Perner et al. | |

FOREIGN PATENT DOCUMENTS

| | | |
|---|---|---|
| DE | 1152536 B | 8/1963 |
| DE | 102009054516 A1 | 6/2011 |
| DE | 102010063923 A1 | 6/2012 |
| EP | 0219830 A2 | 4/1987 |
| GB | 1040452 A | 8/1966 |
| WO | 9523579 A2 | 9/1995 |
| WO | 2012084339 A2 | 6/2012 |
| WO | 2012084340 A2 | 6/2012 |
| WO | 2014111578 A1 | 7/2014 |
| WO | 2015022259 A1 | 2/2015 |
| WO | 2017165931 A1 | 10/2017 |
| WO | 2018218009 A2 | 11/2018 |

OTHER PUBLICATIONS

International Search Report and Written Opinion dated Jul. 9, 2018 for corresponding PCT Application No. PCT/US2018/029797.
International Search Report and Written Opinion for counterpart Application No. PCT/US2019/068978, dated Apr. 8, 2020.
International Search Report and Written Opinion for counterpart Application No. PCT/US2019/069040, dated Mar. 27, 2020.
Non-Final Office Action for copending U.S. Appl. No. 16/731,013, dated Nov. 6, 2020.
Final Office Action for copending U.S. Appl. No. 16/731,013, dated Jun. 14, 2021.
International Preliminary Report on Patentability for counterpart Application No. PCT/US2019/068978, dated Jul. 15, 2021.
International Preliminary Report on Patentability for counterpart Application No. PCT/US2019/069040, dated Jul. 15, 2021.

* cited by examiner

*Primary Examiner* — Nannette Holloman
(74) *Attorney, Agent, or Firm* — McNees Wallace & Nurick LLC

(57) ABSTRACT

A hair treatment composition in a cationic system includes water and a novel association of polysaccharide, such as inulin, a wax, such as, candelilla wax, a cationic surfactant, such as, behentrimonium chloride, and a film-forming polymer, such as polysilicone-29. The composition may include one or more additional components selected from fatty compounds, cationic polymers and styling polymers, embodied to deliver one or more of smoothing, straightening and curling/curl defining style features to achieve a particular straight or curly style with frizz control, softness and manageability.

22 Claims, No Drawings

COMPOSITIONS CONTAINING POLYMERS, WAX, AND CATIONIC SURFACTANT FOR CONDITIONING AND STYLING HAIR

TECHNICAL FIELD

The instant disclosure relates to compositions, kits, and methods for treating hair including, for example, compositions, kits, and methods for conditioning hair to impart conditioning and styling including beneficial properties such as frizz control and hair manageability that include softness, smoothing, good combing properties, and retention of shape and through one or more shampoos.

BACKGROUND

Many different types of hair styling products are commercially available that are aimed to help consumers achieve a desired look, including one or more of fuller hair, thicker hair, sleek and straight hair, frizz-free hair, and defined curls. These products are typically provided in forms that are applied after the shampooing and conditioning processes are completed. Consumers selected from traditional styling products that provide styling benefits such as shaping memory, hold, increased volume, and the like in order to achieve a desired look.

In one example, styling products are available that provide protection against external factors such as protection from moisture to minimize or reduce frizziness. To achieve this benefit, a water-resistant film or coating may be applied to the hair using film-forming polymers. Depending on the chemical make-up of the film-forming polymers. Product formulations that include these polymers can tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or "crunchy" feeling (i.e. the films become hard and brittle and therefore have a crunchy feel or sound when manipulated), which is undesirable to many consumers.

Increasingly, consumers seek hair products that have a natural look and feel, impart good styling benefits to hair, are durable, and lack the drawbacks of current products, such as the stiff and crunchy effects created by the thick coatings of many styling products. Further, consumers seek products that offer multiple benefits, for example, combining frizz reduction and style hold with softening, straightening and curl definition. Thus, there is a need for styling products that can confer the benefits sought by consumers using more natural ingredients and in products that complement the shampooing, conditioning and styling requirements of their customers.

BRIEF SUMMARY

The instant disclosure relates to a water-based hair care composition that includes a unique combination of components that function to impart desirable cosmetic properties to the hair and are delivered during the shampooing and conditioning process, in particular in a cationic system.

In accordance with the various embodiments, the hair care composition is useful for providing a faster routine with fewer steps to achieve style, and the benefits of long-lasting style with a natural look and feel. In particular, the benefits realized include but are not limited to frizz control, shape, discipline, style memory, and hair alignment to achieve looks that include hair smoothing, straightening, softening, and curl definition styling benefits. Also, consumers find the natural look and feel of hair treated with the compositions to be very appealing. In the various embodiments, that may include one or more additional components selected from fatty compounds, cationic polymers and styling polymers, the composition may be embodied to deliver one or more of smoothing, straightening and curling/curl defining style features.

The composition according to the disclosure comprises, in various embodiments, a cationic system that includes water and a novel association of polysaccharide, for example, inulin, a wax, for example, candelilla wax, a cationic surfactant, for example, behentrimonium chloride, and at least one a film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane, for example polysilicone-29. This novel association exhibits synergy to create a hydrophobic film on the hair that confers softening and styling control to achieve styles that include one or more of hair smoothing, straightening, defined curl, and damage protection with a long-lasting effect. In the various embodiments, that may include one or more additional components selected from fatty compounds, cationic polymers and styling polymers, the composition may be embodied to deliver one or more of smoothing, straightening and curling/curl defining style features to achieve a particular straight or curly style with frizz control, softness and manageability.

In accordance with the various embodiments, hair care composition typically includes:
 a. at least one polysaccharide;
 b. at least one wax;
 c. at least one cationic surfactant;
 d. at least one film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane; and
 e. water.

In some embodiments, the composition is an oil in the form of an water emulsion. In some embodiments, the at least one polysaccharide is a plant gum selected from inulin, carrageenan, and pullulan and combinations thereof; the at least one wax is candelilla wax; the at least on one cationic surfactant is behentrimonium chloride, and the at least one film-forming aminosilicone polymer is polysilicone-29.

In some embodiments, the composition comprises at least one fatty alcohol. In some particular embodiments, the composition the least one fatty alcohol comprises one or a combination of selected from cetearyl alcohol (cetyl alcohol and stearyl alcohol), cetyl alcohol stearyl alcohol, behenyl alcohol, and lauryl alcohol. In some specific embodiments, the at least one fatty alcohol comprises cetearyl alcohol.

In some embodiments, the composition comprises at least one fatty compound other than fatty alcohols. In some particular embodiments, the fatty compounds comprise one or a combination of *Ricinus communis* (castor) seed oil, butyrospermum parkii (shea) butter, cetyl esters, C15-19 alkane, and *Elaeis guineensis* (palm) oil.

In some embodiments, the at least one polysaccharide is present in an amount from about 0.2% to about 10% by weight of the composition; the at least one wax is present in an amount from about 0.1% to about 10% by weight of the composition; the at least on one cationic surfactant is present in an amount from about 0.5% to about 10% by weight of the composition; and the at least one film-forming aminosilicone polymer is present in an amount from about 0.5% to about 20% by weight of the composition. In some embodiments, the at least one fatty compound other than fatty alcohols is present from about 0.1% to about 10% by weight of the composition.

In some embodiments, the at least one fatty alcohol is present in an amount from about 0.1% to about 20% by weight of the composition.

In some embodiments, the composition comprises a cosmetically acceptable carrier comprising water and one or more water soluble solvents. In some particular embodiments, the water-soluble solvents may include polyols and short chain mono-alcohols. In some specific embodiments the water-soluble solvents are selected from glycerin, propylene glycol, butylene glycol, and combinations thereof.

In some embodiments, the composition comprises one or a combination of cationic polymers. In some particular embodiments, the cationic polymers are selected from polyquaternium-6, polyquaternium-46, polyquaternium-37, and hydroxypropyl guar hydroxypropyltrimonium chloride. In some embodiments, the one or a combination of cationic polymers is present from about 0.1% to about 10% by weight of the composition.

In some embodiments, the composition comprises one or a combination of nonionic polymers. In some particular embodiments, the nonionic polymers are selected from hydroxypropyl guar and/or potato starch modified. In some embodiments, the one or a combination of nonionic polymers is present from about 0.1% to about 10% by weight of the composition In some embodiments, the composition comprises one or more styling polymers. In some particular embodiments, the one or more styling polymers comprise vp/va copolymer, vp/dimethylam inoethylmethacrylate copolymer, and acrylamidopropyltrimonium chloride/acrylates copolymer (available in combination isohexadecane (and) coceth-7). In some embodiments, the one or a combination of cationic polymers, nonionic polymers, and styling polymers is present from about 0.1% to about 10% by weight of the composition.

Additional components such as active compounds, fragrance, preservatives may be included. In some embodiments, the composition comprises potassium hydroxide; sodium hydroxide; acetamide mea; lactic acid; taurine; citric acid; gluconolactone; fragrance; one or more preservatives comprising chlorhexidine dihydrochloride, phenoxyethanol, benzoic acid; one or more silicone compounds comprising lauryl PEG/PPG-18/18 methicone, dimethicone (and) dimethiconol, amodimethicone (and) trideceth-6 (and) cetrimonium chloride, am inopropyl triethoxysilane, dimethicone (and) amodimethicone in combination with trideceth-10 (and) PEG-100 stearate (and) steareth-6 (and) trideceth-3; and combinations thereof.

The hair care composition, in various embodiments, is unique in the ability to provide hair with improved manageability, long-lasting style and frizz control, and protection. Accordingly, the instant disclosure relates to methods for treating hair, for example, for improving the manageability of hair, for imparting lasting style and frizz control. More specifically, the hair care compositions may be used in methods for conditioning the hair, providing curl definition to the hair, providing frizz control to the hair, improving ease of combability and detangling, protecting the hair from damage, including heat damage, and increasing the appearance of hair volume.

The methods of treating hair according to the disclosure include application of the compositions of the present disclosure to shampooed hair, together or mixed with a conventional conditioner followed by rinsing from the hair, or in place of the conventional conditioner (and optionally followed with a treatment with a conventional conditioner), or after application and rinsing of a conventional conditioner, all optionally followed by rinsing.

DESCRIPTION

The composition in accordance with the disclosure provides unexpected and lasting benefits for hair styling when used as a rinse off product incorporated into a cationic based oil in water conditioner system. The unexpected benefits realized include but are not limited to frizz control, shape, discipline, style memory, and hair alignment to achieve looks that include hair smoothing, straightening, softening, and curl definition.

Managing, controlling, styling hair is something consumers must deal with on a daily basis, which typically involves daily time commitments to shampoo, condition, and style, which may include one or more of blow-dry and flat iron use in order to achieve a desired look. With the help of traditional hair styling products such as gels, mousse, sprays, creams, waxes, paste, balms and serums the desired style can be achieved, but they constitute additional steps in grooming the hair after the shampooing/conditioning process.

To address this context, a built-in treatment product that can provide styling, shaping, and manageability benefits to hair during the shampooing/conditioning process has been developed, as described herein. The composition according to the instant disclosure, embodied in a conditioner system or used in between a shampoo and a conditioner, enables a lifestyle enhancement for consumers by providing a novel rinse-off styling technology for hair care and styling. The composition, in various embodiments, includes components which create a hydrophobic film on the hair that imparts one or more of benefits. The composition can be used in the shower/shampooing care process as a combined conditioning and hair styling treatment which imparts softness, smoothing, good combing properties, and after drying hair, keeps hair soft, styled, shaped and smooth feeling with a long-lasting benefit that is retained through at least one shampooing, wherein shaping includes one or more of straightening and curling. Accordingly, the composition allows a consumer to have a simplified routine, integrating conditioning with styling and style manageability. The composition also provides protection to the hair from damage, for example, damage caused by heat, environmental stress, etc. And the benefits of the composition, in the various embodiments, are long lasting, as styled hair treated with the composition can survive washing or rinsing. Thus, hair maintains the desirable cosmetic properties imparted by the hair care compositions until the next shampooing, rinsing, etc.

Salon trials have shown that the composition, in various embodiments, delivers unexpected performance that includes long lasting style, ease of styling, frizz control, and enables the consumer to achieve hair styling with a natural look and feel without crunch. Also, unexpectedly, the composition provides a "salon grade" look, that includes smoothing the hair and retained holding of style longer, i.e., even after rinsing the hair; the hair looks shiny, soft and smooth from root to tip, it also aligns the hair from root to tip. Further, as described in the exemplified embodiments, the styling compositions show a benefit for a wide range of curl patterns and demographics, providing for well defined, frizz free curls that unexpectedly exceed consumers' expectations in delivering superior long-lasting benefits. Hair is easy to detangle, soft, shiny, bouncy with movement, including well-defined curls and no frizz.

The composition according to the disclosure comprises, in various embodiments, water that is, in some embodiments, present at a level of at least 20%, or at least 50%, or at least 70% by weight of composition. The composition also includes in a cationic system a novel association of polysaccharide, for example, Inulin, a wax, for example, candelilla wax, a cationic surfactant, for example, Behentrimonium Chloride, and at least one a film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane, for example polysilicone-29. This novel association exhibits synergy to create a hydrophobic film on the hair that confers softening and styling control to achieve styles that include one or more of hair smoothing, straightening, defined curl, and damage protection with a long-lasting effect.

In an embodiment, the composition of the present disclosure is in the form of an oil-in-water emulsion and includes at least one fatty alcohol. In the various embodiments, the composition of the present disclosure may include one or more additional components selected from fatty compounds other than fatty alcohols, cationic polymers, nonionic polymers, styling polymers, and silicone compounds and the composition may be embodied to deliver one or more of smoothing, straightening and curling/curl defining style features, in particular, during the shampooing and conditioning process.

In an embodiment, the composition of the present disclosure is a rinse-off composition, i.e., the composition is washed off the hair after the hair is contacted with the composition. In an embodiment, the composition of the present disclosure is allowed to remain on the hair for at least 30 second, or up to 30 minutes, before it is rinsed off the hair.

While not wishing to be bound by any particular theory, it is posited that the compositions provide the hair with a hydrophobic, flexible, film or film-like coating that is long-lasting, has a very natural look and feel, and improves the styling properties of the hair. The compositional components that include the polysaccharide and the film-forming polymer contribute to the lightweight texture and provides the smooth hair feel, while the wax helps with the shaping of the hair to confer one or more of straight and smooth hair and defined curls, while the cationic surfactant provides the antistatic properties to hair and also acts as a hair conditioning agent. When the composition of the present disclosure is in the form of an oil-in-water emulsion, at least one fatty alcohol is present which helps with the formation of a stable emulsion. Addition of fatty compounds other than fatty alcohols and one or more of cationic polymers, nonionic polymers, styling polymers, and silicones confer additional benefits to achieve styling and control of one or more of hair smoothing and curl definition.

The hair care composition can be used at home during an individual's regular shampooing and/or conditioning routine and therefore do not require special procedures that are only available at professional salons. Accordingly, the instant disclosure relates to individual products that comprise the composition in a conditioner vehicle, and kits that include a hair care composition of the instant disclosure together with other compositions. The kits typically include at least one hair care composition according to the instant disclosure (a hair care composition comprising one or more polysaccharides, one or more waxes, one or more cationic surfactants, one or more film-forming silicone polymers, and water, etc.) and one or more additional hair care compositions, for example, a shampoo and/or a conditioner. The various hair care compositions are separately contained in the kits. In some instances, the kits include one or more hair care compositions (according the instant disclosure) and a shampoo and/or a conditioner, each of which are separately contained.

(a) Polysaccharide

In accordance with the disclosure, the hair care composition includes in the various embodiments at least one polysaccharide. In general, the polysaccharide may be chosen from polysaccharides isolated from algae, polysaccharides produced by microorganisms, and polysaccharides from higher plants, such as homogeneous polysaccharides. In particular, the polysaccharides may be chosen from fructans, galactans, pullulan, and derivatives thereof. In other examples, the polysaccharides may comprise methylcelluloses, hydroxyalkylcelluloses, ethylhydroxyethylcelluloses and carboxymethylcelluloses, mannans, xylans, lignins, arabans, galacturonans, alginate-based compounds, chitin, chitosans, glucuronoxylans, arabinoxylans, xyloglucans, glucomannans, pectic acids and pectins, arabinogalactans, agars, glycosaminoglycans, gum arabics, tragacanth gums, ghatti gums, karaya gums, locust bean gums, galactomannans such as guar gums and nonionic derivatives thereof, in particular hydroxypropyl guar, and ionic derivatives thereof, biopolysaccharide gums of microbial origin, in particular scleroglucan or xanthan gums, mucopolysaccharides, and in particular chondroitin sulfates, and mixtures thereof.

In some embodiments, the at least one polysaccharide may be chosen from fructans, galactans, pullulan, derivatives thereof and combinations thereof.

According to the various embodiments, the at least one polysaccharide may be chemically modified, especially with urea or urethane groups, or by a hydrolysis, oxidation, esterification, etherification, sulfatation, phosphatation, amination, amidation or alkylation reaction, or by several of these modifications. The derivatives obtained may be anionic, cationic, amphoteric or nonionic.

Polysaccharides Isolated from Algae: Fructosans

In some particular embodiments, the polysaccharide according to the invention may especially be a fructosan chosen from inulin and derivatives thereof (especially dicarboxy and carboxymethyl inulins). Fructans or fructosans are oligosaccharides or polysaccharides comprising a sequence of anhydrofructose units optionally combined with several saccharide residues other than fructose. Fructans may be linear or branched. Fructans may be products obtained directly from a vegetable or microbial source or alternatively products whose chain length has been modified (increased or decreased) by fractionation, synthesis or hydrolysis, in particular enzymatic. Fructans generally have a degree of polymerization from 2 to about 1000 and, in some embodiments, from 2 to about 60.

Three groups of fructans are distinguished. The first group corresponds to products whose fructose units are for the most part linked via β(2,1) bonds. These are essentially linear fructans such as inulins. The second group also corresponds to linear fructoses, but the fructose units are essentially linked via β(2,6) bonds. These products are levans. The third group corresponds to mixed fructans, i.e. fructans containing β(2,6) and β(2,1) sequences. These are essentially branched fructans, such as graminans. Inulin is also referred to technically as Alantin, Fructosane, Synantherin, and Synanthrin Inulin may be obtained, for example, from chicory, dahlia or Jerusalem artichoke, in some embodiments, from chicory. Inulin is the polysaccharide that conforms to the formula:

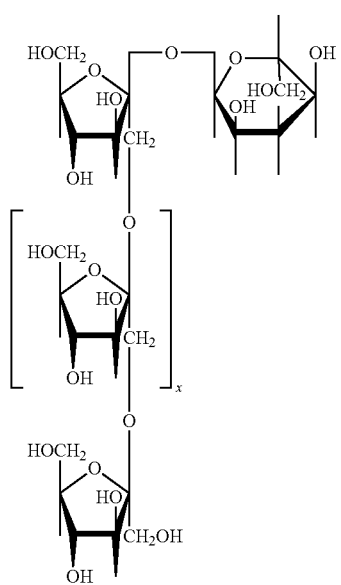

(I)

In particular, the polysaccharide, especially the inulin, has a degree of polymerization from 2 to about 1000 and, in some embodiments, from 2 to about 60, and a degree of substitution of less than 2 on the basis of one fructose unit. The inulin used for this invention is represented, for example, by the products available under the tradename INUTEC H25P (CREACHEM), also sold under the name Beneo™ Inulin by the company Orafti, and under the name Frutafit® by the company Sensus.

TABLE 1

Inulin Properties vs Polyurethane and PVP

| Property | Inulin | PU34 | PVP |
|---|---|---|---|
| Hardness (flexibility; three-point bending test) | 40.75 | 70 | 203.25 |
| Hydrophobicity (Contact Angle) | 117.84 | 91.45 | 57.11 |

Polysaccharides Isolated from Algae: Galactans

In some particular embodiments, the polysaccharide according to the invention may be a galactan chosen especially from agar and carrageenans. Galactans of agar type are galactose polysaccharides contained in the cell wall of some of these species of red algae (Rhodophyceae) belonging to the Gigartinaceae, Hypneaceae, Furcellariaceae and Polyideaceae families. They are formed from a polymer group in which the base backbone is a β(1,3) D-galactopyranose and α(1,4) L 3-6 anhydrogalactose chain, these units repeating regularly and alternately. The differences within the agar family are due to the presence or absence of methyl or carboxyethyl solvated groups. These hybrid structures are generally present in variable percentage, depending on the species of algae and the season of harvest.

They are generally obtained by hot aqueous extraction from natural strains of the said algae. These linear polymers, formed by disaccharide units, are composed of two D-galactopyranose units alternately linked via α(1,3) and β(1,4) bonds. These are highly sulfated polysaccharides (20-50%) and the α-D-galactopyranosyl residues may be in 3,6-anhydro form. According to the number and position of the ester sulfate groups on the repeat disaccharide of the molecule, several types of carrageenan are distinguished, namely: kappa-carrageenans, which bear one ester sulfate group, iota-carrageenans which bear two ester sulfate groups, and lambda-carrageenans which bear three ester sulfate groups.

Carrageenans are composed essentially of potassium, sodium, magnesium, triethanolamine and/or calcium salts and of ester sulfates of polysaccharides. Carrageenans are sold especially by the company SEPPIC under the name Solagum®, by the company Gelymar under the names Carragel®, Carralact® and Carrasol®, by the company Cargill under the names Satiagel™ and Satiagum™, and by the company CP-Kelco under the names Genulacta®, Genugel® and Genuvisco®.

Polysaccharides Produced by Microorganisms: Pullulan

In some particular embodiments, the polysaccharide according to the invention may be pullulan. Pullulan is a polysaccharide consisting of maltotriose units, known under the name α(1,4)-α(1,6)-glucan. Three glucose units in maltotriose are connected via an α(1,4) glycosidic bond, whereas the consecutive maltotriose units are connected to each other via an α(1,6) glycosidic bond. Pullulan is produced, for example, under the reference Pullulan PF 20 by the company Hayashibara in Japan.

In general, the compounds of this type that may be used in the present invention are chosen from those described especially in Kirk-Othmer's *Encyclopedia of Chemical Technology*, Third Edition, 1982, volume 3, pp. 896-900, and volume 15, pp. 439-458, in *Polymers in Nature* by E. A. McGregor and C. T. Greenwood, published by John Wiley & Sons, Chapter 6, pp. 240-328, 1980, in the publication by Robert L. Davidson entitled *Handbook of Water-soluble Gums and Resins* published by McGraw-Hill Book Company (1980) and in *Industrial Gums—Polysaccharides and their Derivatives*, edited by Roy L. Whistler, Second Edition, published by Academic Press Inc.

In accordance with the various embodiments, the amount of each of the at least one polysaccharide present in the compositions can range from about 0.5% to about 10%, or from about 0.5% to about 7%, or from about 1% to about 3.5% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of polysaccharide present in the compositions can range from about 0.2% to about 20%, or from about 0.4% to about 10%, or from about 0.5% to about 5%, or from about 1% to about 3% or any suitable combination, sub-combination, range, or sub-range thereof by weight, based on the weight of the composition. One of ordinary skill in the art, however, will appreciate that other ranges are within the scope of the invention.

Thus, any one of the at least one polysaccharide is present, by weight, based on the total weight of the composition, from about 0.2, 0.3, 0.4, 0.5, 0.6, 0.7, 0.8, 0.9, 1, 2, 3, 4, 5, 6, 7, 8, 9, to about 10 weight percent, including increments and ranges therein and there between.

(b) Wax

In accordance with the disclosure, the hair care composition includes in the various embodiments at least one wax. The at least one wax may be the form of a mixture of waxes. In the various embodiments, wax is generally a lipophilic compound that is solid at room temperature (25° C.), with a solid/liquid reversible change of state, having a melting point of greater than or equal to 45° C. in some embodiments, ranging from 45 to 95° C. and more particularly ranging from 45 to 85° C. Thus, the at least one wax is chosen from waxes with a melting point of greater than 45° C. comprising esters having a chain length of one or more C4o-C7o ester compounds and not comprising any C20-C39 ester compounds.

The content of ester comprising from 40 to 70 carbon atoms and, in some embodiments, ranges from 20% to 100% by weight and, in some embodiments, from 20% to 90% by weight relative to the total weight of wax(es). Candelilla wax is derived from the leaves of the Mexican shrub *Euphorbia antisyphilitica*. Candelilla wax is obtained from a shrub named *Euphorbia Cerifera*, indigenous to northern Mexico. The wax protects the plant against the environment and prevents excessive evaporation. Candelilla wax consists of hydrocarbons (ca. 50%, C29-C33, mainly C31), esters, phytosterols, free fatty acids, free fatty alcohols and resins. Candelilla wax has a high oil binding capacity and is less sticky than beeswax. It is used to adjust viscosity in water-in-oil emulsions. It imparts gloss and hardness in cosmetic products such as hair wax and lipstick. Candelilla wax contains up to 45% hydrocarbons and 20-30% fatty esters. NCI name: *Euphorbia cerifera* cera; Melting point: 68-73° C.

Sunflower wax is obtained by dewaxing sunflower oil. Sunflower wax has a high oil binding capacity and a non-sticky skin feel. It imparts gloss to formulations and stabilizes water-in-oil emulsions. This wax contains approximately 30% hydrocarbons and 70% fatty esters. Behenyl acetate, lignoceryl acetate and methyl lignocerate are the main wax esters. INCI name: *Helianthus annuus* seed cera, Melting point: 74-80° C.

In some particular embodiments, the at least one wax comprises one or candelilla wax, sunflower wax and combinations thereof.

In accordance with the various embodiments, the amount of each of the at least one wax is from about 0.1% to about 10%, or from about 0.2% to about 4%, or from about 0.3% to about 3%, or from about 0.5% to about 2.5% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of wax present in the compositions can range from about 0.1% to about 20%, or from about 0.5% to about 10%, or from about 1% to about 5% or any suitable combination, sub-combination, range, or sub-range thereof by weight, based on the weight of the composition. One of ordinary skill in the art, however, will appreciate that other ranges are within the scope of the invention.

Thus, any one of the at least one wax is present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9, to about 10 weight percent, including increments and ranges therein and there between.

(c) Cationic Surfactant

In accordance with the disclosure, the hair care composition includes in the various embodiments at least one cationic surfactant. The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some embodiments, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

In some embodiments, the cationic surfactants are selected from cetrimonium chloride, behentrimonium chloride, behentrimonium methosulfate, stearamidopropyl dimethylamine, and a mixture thereof.

In some particular embodiments, the cationic surfactant comprises cetrimonium chloride, behentrimonium chloride, and mixtures thereof. Behentrimonium Chloride, also described by the technical names that include 1-Docosanaminium, N,N,N-Trimethyl-, Chloride, and N,N,N-Trimethyl-1-Docosanaminium Chloride, is the quaternary ammonium salt that conforms to the formula:

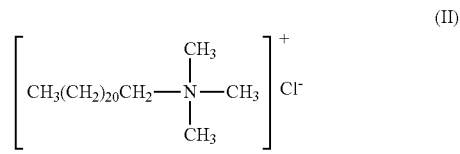

A more exhaustive list of cationic surfactants that may be included in the hair care compositions is provided later, under the heading "Cationic Surfactants."

In accordance with some embodiments, the amount of each of the at least one cationic surfactant is from about 0.5% to about 10%, or from about 0.5% to about 8%, or from about 1% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of cationic surfactant present in the compositions can range from about 0.5% to about 20%, or from about 0.5% to about 10%, or from about 0.5% to about 5%, or from about 1% to about 3% or any suitable combination, sub-combination, range, or sub-range thereof by weight, based on the weight of the composition. One of ordinary skill in the art, however, will appreciate that other ranges are within the scope of the invention.

Thus, any one of the at least one cationic surfactant is present, by weight, based on the total weight of the composition, from about 0.5, 0.6, 0.7, 0.8, 0.9, 1, 2, 3, 4, 5, 6, 7, 8, 9, to about 10 weight percent, including increments and ranges therein and there between.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and mixtures thereof.

In some cases, it is useful to use salts such as chloride salts of the quaternary ammonium compounds.

The fatty amines generally comprise at least one $C_8$-$C_{30}$ hydrocarbon-based chain.

A. Examples of quaternary ammonium salts that may especially be mentioned include: those corresponding to the general formula (III) below:

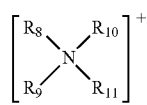

(III)

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and, in some embodiments, from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy ($C_2$-$C_6$)alkylene, $C_1$-$C_{30}$ alkylamide, ($C_{12}$-$C_{22}$)alkylamido ($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

B. a quaternary ammonium salt of imidazoline, such as, for example, those of formula (IV) below:

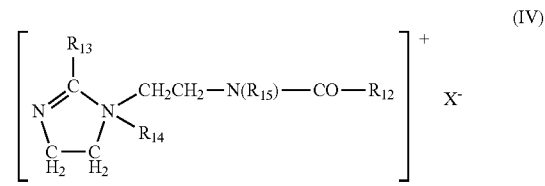

(IV)

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups, in some embodiments, comprise, respectively, from 1 to 20 carbon atoms and from 6 to 30 carbon atoms. $R_{12}$ and $R_{13}$, in some embodiments, denote a mixture of alkenyl or alkyl groups containing from 12 to 21 carbon atoms, derived for example from tallow fatty acids, $R_{14}$, in some embodiments, denotes a methyl group, and $R_{15}$, in some embodiments, denotes a hydrogen atom. Such a product is sold, for example, under the name REWOQUAT W 75 by the company Rewo;

C. a quaternary diammonium or triammonium salt, in particular of formula (V):

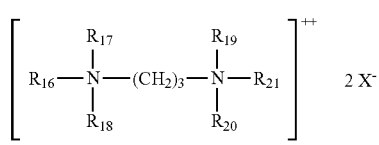

(V)

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), D. Cationic/cationizable surfactants, for example of the general structure R4-A-R5-B wherein R4 is a saturated or unsaturated, straight or branched alkyl chain with 8 to 24 C atoms, R5 is a straight or branched alkyl chain with 1 to 4 C atoms, A is selected from:

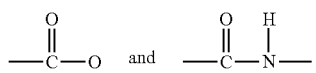

and B is selected from

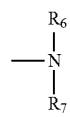

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms,

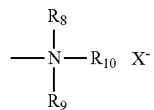

$R_8$ and $R_9$ are the same or different, an alkyl chain with 1 to 4 atoms, hydroxyl alkyl chain with 1 to 4 C atoms and di hydroxyl alkyl chain with 2 to 4 C atoms, R.sub.10 is an alkyl chain with 1 to 4 C atoms, hydroxyl alkyl chain with 1 to 4 C atoms or di hydroxyl alkyl chain with 2 to 4 C atoms.

In some instances, $R_4$ is saturated, straight or branched alkyl chain with 10 to 24 C atoms, in some embodiments, 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidpropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearmidopropyl dimethylamine, steramidopropyl diethylamine, stearmidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxypropylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibenhenamidopropyl propylamine, dibehenamidopropyl hydroxyethylamine, palmitoamidopropyl trimethyl ammonium chloride, stearamidopropyl trimethylammonium chloride, behenamidopopyl tri hydroyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxypropylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropy hydroxypropylamine, stearoylpropyl amine, stearoylpropyl methylamine, stearoylpropyl diethylamine, stearoylpropyl dibutylamine, stearoylpropyl butylamine, stearolpropyl dipropylamine, behenylpropyl propylamine, behenylpropyl dihydroxyethylamine, behenylpropyl hydroxyethylamine, behenylpropyl diydroxypropylamine, behenylpropyl hydroxypropylamine behenylpropyl amine, behenylpropyl methylamine, behenylpropyl diethylamine, behenylpropyl dibutylamine, behenylpropy butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants or amphiphilic surfactants may be chosen from fatty alkylamines, in some embodiments, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures therefore useful, especially in combination with fatty dimethylamines such as, for example, stearamidopropyl dimethylamine.

(d) Film-Forming Aminosilicone Polymer

In accordance with the disclosure, the hair care composition includes in the various embodiments at least one film-forming aminosilicone polymer.

In accordance with some particular embodiments, the composition includes at least one a film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane.

In accordance with some embodiments, the at least one film-forming am inosilicone polymer comprises Polysilicone-29, which is a film-forming am inosilicone polymer formed by the reaction between a glycidoxypropyl-terminated dimethyl siloxane polymer, PEG-13 diglycidyl ether, diethylaminopropylamine, and aminopropyltriisopropoxysilane sold under the tradename SILSOFT CLX-E emulsion (Momentive Performance Materials).

In accordance with the various embodiments, the amount of each of the at least one film-forming aminosilicone polymer is from about 0.5% to about 20%, or from about 0.5% to about 15%, or from about 1% to about 10%, or from about 2% to about 5% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of film-forming aminosilicone polymer present in the compositions can range from about 0.5% to about 40%, or from about 0.5% to about 20%, or from about 0.5% to about 10%, or from about 1% to about 5% or any suitable combination, sub-combination, range, or sub-range thereof by weight, based on the weight of the composition. One of ordinary skill in the art, however, will appreciate that other ranges are within the scope of the invention.

Thus, any one of the at least one film-forming aminosilicone polymer is present, by weight, based on the total weight of the composition, from about 0.5, 0.6, 0.7, 0.8, 0.9, 1, 2, 3, 4, 5, 6, 7, 8, 9, 10, 11, 12, 13, 14, 15, 16, 17, 18, 19, to about 20 weight percent, including increments and ranges therein and there between.

(e) Water/Cosmetically Acceptable Carrier

In accordance with the disclosure, the hair care composition includes in the various embodiments, water, and in some embodiments, one or more water-soluble solvents, or mixtures thereof in a cosmetically acceptable carrier.

Water

In accordance with the various embodiments water is present in total amounts of from about 20%, or from about 40%, or from about 50%, or from about 60%, or from about 65%, or from about 70%, or from about 75%, or from about 80%, or from about 85%, or from about 90%, and up to about 99%, or up to about 95%, or up to about 90%, or up to about 85%, or up to about 80%, or up to about 75%, or up to about 70%. For example, water is present in amounts ranging from about 60% to about 99% by weight, about 70% to about 95% by weight, or about 60%, 70%, 75%, 80%, 85%, 90%, 95%, or 99% by weight, or any suitable combination, sub-combination, range, or sub-range thereof by weight, based on the weight of the composition. One of ordinary skill in the art, however, will appreciate that other ranges are within the scope of the invention.

Thus, any water is present, by weight, based on the total weight of the composition, from about 20, 30, 40, 50, 60, 61, 62, 63, 64, 65, 66, 67, 68, 69, 70, 71, 72, 73, 74, 75, 76, 77, 78, 79, 80, 85, 90, 95, to about 99 weight percent, including increments and ranges therein and there between.

Water-Soluble Solvents

In accordance with some embodiments, the hair treatment composition may include in the cosmetically acceptable carrier at least one water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), organic solvents, polyols, glycols, or mixtures thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylne glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or mixtures thereof.

In some cases, the water-soluble solvent may be selected from the group consisting of one or more glycols, $C_{1-4}$ alcohols, glycerin, or mixtures thereof, for example, glycerin, ethylhexylglycerin, and mixtures thereof.

In accordance with the various embodiments total amount of the at least one water-soluble solvent, when present, may vary, but is typically from about 0.5% to about 25%, or from about 0.5% to about 20%, or from about 1% to about 20%, or from about 1% to about 10%, or from about 2% to about 5% or any suitable combination, sub-combination, range, or sub-range thereof by weight, based on the weight of the composition. One of ordinary skill in the art, however, will appreciate that other ranges are within the scope of the invention.

Thus, any one water-soluble solvent, when present, is present, by weight, based on the total weight of the composition, from about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between.

Fatty Alcohols

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the hair treatment compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In particular, it is possible to mention, alone or as a mixture: lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol).

Preferably, the solid fatty alcohol is chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C=C double bond) and contain from 12 to 40 carbon atoms.

The liquid fatty alcohols may be represented by: R—OH, wherein R denotes a C12-C24 branched alkyl group or an alkenyl group (comprising at least one C12-C24 double bond C=C), R being optionally substituted by a or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the hair treatment compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the hair treatment compositions preferably include cetearyl alcohol.

The total amount of fatty alcohol(s) in the hair treatment compositions can vary but is typically about 0.1 to about 20 wt. %, based on the total weight of the hair treatment compositions. Similarly, the total amount of fatty alcohol(s) may be about 0.1 to about 15 wt. %, about 0.1 to about 10 wt. %, about 1 to about 20 wt. %, about 1 to about 15 wt. %, about 1 to about 10 wt. %, about 2 to about 20 wt. %, about 2 to about 15 wt. %, about 2 to about 10 wt. %, about 2 wt. %, about 3 wt. %, about 4 wt. %, about 5 wt. %, about 6 wt. %, about 7 wt. %, about 8 wt. %, or about 9 wt. %, including all ranges and subranges therebetween

Fatty Compounds Other than Fatty Alcohols

In accordance with the disclosure, the hair care composition may include in some embodiments one or more fatty compounds. Fatty compounds that may be present include, in some embodiments, "non-silicone fatty compounds," i.e., fatty compounds that do not containing any silicon (Si) atoms. Non-limiting examples of non-silicone fatty compounds include oils, mineral oil, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, or mixtures thereof. Non-limiting examples of the fatty acids, fatty alcohol derivatives, and fatty acid derivatives are found in International Cosmetic Ingredient Dictionary, Sixteenth Edition, 2016, which is incorporated by reference herein in its entirety.

In some embodiments, fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, or mixtures thereof. In some cases, the fatty acids are selected from the group consisting of palmitic acid, stearic acid, or mixtures thereof.

Fatty alcohol derivatives include alkyl ethers of fatty alcohols, alkoxylated fatty alcohols, alkyl ethers of alkoxylated fatty alcohols, esters of fatty alcohols or mixtures thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e., a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; or mixtures thereof.

Non-limiting examples of polyglycerol esters of fatty acids include those of the following formula (XVII):

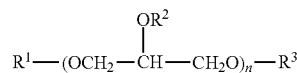

(VI)

wherein:
the average value of n is about 3; and
$R^1$, $R^2$, and $R^3$, which may be identical or different, are independently chosen from a fatty acid moiety or hydrogen, provided that at least one of $R^1$, $R^2$, and $R^3$ is a fatty acid moiety.

For instance, $R^1$, $R^2$ and $R^3$ may be saturated or unsaturated, straight or branched, and have a length of $C_1$-$C_{40}$, $C_1$-$C_{30}$, $C_1$-$C_{25}$, $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, or mixtures thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, or mixtures thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, or mixtures thereof. Preferred for use herein are glycerol monostearate, 12-hydroxy stearic acid, or mixtures thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, or 50° C. or higher. The high melting point fatty compound may be selected from fatty acids, fatty alcohol derivatives, fatty acid derivatives, or mixtures thereof. Nonlimiting examples of the high melting point compounds are found in the International Cosmetic Ingredient Dictionary, Sixteenth Edition, 2016, which is incorporated by reference herein in its entirety.

In some embodiments, the non-silicone fatty compounds include one or more non-silicone oils. The term "oil" as used herein describes any material which is substantially insoluble in water. Suitable non-silicone oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Suitable low viscosity oils have a viscosity of 5-100 mPas at 25° C. and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isodecanol, polyglyceryl-3-diisostearate, or combinations thereof. The high viscosity oils generally have a viscosity of 200-1,000,000, or 100,000-250,000, mPas at 25° C. Such oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

In accordance with the various embodiments, when present, the amount of each of the at least one fatty compound is from about 0.1% to about 10%, or from about 0.1% to about 8%, or from about 0.2% to about 7%, or from about 1% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of fatty compound present in the compositions can range from about 0.1% to about 15%, or from about 0.5% to about 12%, or from about 1% to about 10%, or from about 1.5% to about 5% or any suitable combination, sub-combination, range, or sub-range thereof by weight, based on the weight of the composition. One of ordinary skill in the art, however, will appreciate that other ranges are within the scope of the invention.

Thus, any one of the at least one fatty compound is present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9, to about 10 weight percent, including increments and ranges therein and there between.

Cationic Polymers

In accordance with the disclosure, the hair care composition may include in the various embodiments at least one cationic polymer.

Non-limiting examples of cationic polymers include poly (methacryloyloxyethyl trimethylammonium chloride), polyquaternium-6, polyquaternium-37 (and) propylene glycol dicaprylate/dicaprate (and) PPG-1 trideceth-6, polyquaternium-46, quaternized cellulose derivatives, polyquaternium-4, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In some instances, the one or more cationic polymers may be selected from the group consisting of polyquaternium-4, polyquaternium-10, cationic guar derivatives, and a mixture thereof.

The cationic polymers can be a monoalkyl quaternary amine, such as stearyltrimonium chloride, soyatrimonium chloride or coco-ethyldimonium ethosulfate. Other suitable cationic polymers include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic polymers may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, am inopropyl dimethicone, Quaterium-8, and dilinoleamidopropyl dimethylamine dimethicone PEG-7 phosphate.

In some instances, the cationic polymers are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryoloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases, quaternized polymeric cationic polymers are particularly useful. Some cationic polymers are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 is sold under the trademark MERQUAT-100 and is described as having a weight average molecular weight of approximately 100,000. A copolymer reaction product of dimethyldiallylammonium chloride with acrylamide monomers is named Polyquaternium-7 is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10. Also useful are quaternized copolymers of hydroxyethylcellulose and dimethyldimethylammonium chloride, having the name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the name for a chemically modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

In some particular embodiments, the at least one cationic polymer comprises one of Polyquaternium-6, Polyquaternium-46, and Polyquaternium-37 (and) propylene glycol dicaprylate/dicaprate (and) PPG-1 trideceth-6, and combinations thereof.

In accordance with the various embodiments, the amount of each of the at least one cationic polymer is from about 0.1% to about 10%, or from about 0.1% to about 8%, or from about 0.2% to about 7%, or from about 1% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of cationic polymer present in the compositions can range from about 0.1% to about 15%, or from about 0.5% to about 12%, or from about 1% to about 10%, or from about 1.5% to about 5% or any suitable combination, sub-combination, range, or sub-range thereof by weight, based on the weight of the composition. One of ordinary skill in the art, however, will appreciate that other ranges are within the scope of the invention.

Thus, any one of the at least one cationic polymer is present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9, to about 10 weight percent, including increments and ranges therein and there between.

Additional Cationic Styling Polymers; Other Polymers

In accordance with the disclosure, the hair care composition may include in the various embodiments at least one styling polymer.

Non-limiting examples of styling polymers include polyacrylate crosspolymers or crosslinked polyacrylate polymers, cationic acrylate copolymers, anionic acrylic or carboxylic acid polymers, carbomers, polyacrylamide polymers, gums, vinylpyrrolidone homopolymers/copolymers, and mixtures thereof. Non-limiting examples of styling polymers include anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CAR- BOPOL Aqua SF-1 (Lubrizol), INCI name: acrylates crosspolymer-4, sold under the tradename CARBOPOL Aqua SF-2 (Lubrizol), and a mixture thereof. In some particular embodiments, the at least one styling polymer comprises hydroxypropyl guar hydroxypropyltrimonium chloride, hydroxypropyl guar, potato starch modified, VP/VA copolymer, VP/dimethylaminoethylmethacrylate copolymer, and acrylamidopropyltrimonium chloride/acrylates copolymer (and) isohexadecane (and) coceth-7, and combinations thereof. In some embodiments, the compositions may also include one or more additional polymers such as thickening polymers, for example selected from hydroxypropyl guar hydroxypropyltrimonium chloride, hydroxypropyl guar, potato starch modified, and combinations thereof.

In accordance with the various embodiments, when present, the amount of each of the at least one styling polymer is from about 0.1% to about 10%, or from about 0.1% to about 8%, or from about 0.2% to about 7%, or from about 1% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of styling polymer present in the compositions can range from about 0.1% to about 15%, or from about 0.5% to about 12%, or from about 1% to about 10%, or from about 1.5% to about 5% or any suitable combination, sub-combination, range, or sub-range thereof by weight, based on the weight of the composition. One of ordinary skill in the art, however, will appreciate that other ranges are within the scope of the invention.

Thus, any one of the at least one styling polymer is present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9, to about 10 weight percent, including increments and ranges therein and there between.

Silicones

The hair treatment composition of the instant disclosure may optionally include one or more silicones. Nonetheless, in some instances the composition is free or essentially free of silicones. In other words, one or more of the following silicones may be optionally included or optionally excluded from the composition.

Silicones include, but are not limited to, polyorganosiloxanes, polyalkylsiloxanes, polyarylsiloxanes, polyalkarylsiloxanes, polyestersiloxanes, or mixtures thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane or mixtures thereof.

In some instances, the compositions include (or exclude) one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, or mixtures thereof.

In some particular embodiments, the one or more silicone compound comprises one or more silicone compounds comprising lauryl PEG/PPG-18/18 methicone, dimethicone (and) dimethiconol, amodimethicone (and) trideceth-6 (and) cetrimonium chloride, am inopropyl triethoxysilane, dimethicone (and) amodimethicone (and) trideceth-10 (and) PEG-100 stearate (and) steareth-6 (and) trideceth-3, and combinations of these.

In accordance with the various embodiments, when present, the amount of each of the one or more silicone compounds is from about 0.1% to about 8%, or from about 0.2% to about 7%, or from about 1% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, the total amount of silicone compounds present in the compositions can range from about 0.1% to about 15%, or from about 0.5% to about 12%, or from about 1% to about 10%, or from about 1.5% to about 5% or any suitable combination, sub-combination, range, or sub-range thereof by weight, based on the weight of the composition. One of ordinary skill in the art, however, will appreciate that other ranges are within the scope of the invention.

Thus, any one of the one or more silicone compounds is present, by weight, based on the total weight of the composition, from about 0.1, 0.2, 0.3, 0.4, 0.5, 0.6, 0.7, 0.8, 0.9, 1, 2, 3, 4, 5, 6, 7, to about 8 weight percent, including increments and ranges therein and there between.

The hair treatment composition may include (or exclude) one or more silicone oils, for example one or more non-phenyl silicone oils and/or one or more phenyl silicone oils. The silicone oil is, in some embodiments, apolar. An "apolar silicone oil" is intended to denote a silicon oil that does not comprise any ionic or ionisable group(s), and, in some embodiments, does not comprise any oxyalkylenated ($C_2$-$C_4$) unit(s) (, in some embodiments, oxyethylene, oxypropylene), or glycerol unit(s).

Representative examples of non-volatile non-phenyl silicone oils which may be mentioned include polydimethylsiloxanes; alkyl dimethicones; vinylmethyl methicones; and also, silicones modified with aliphatic groups and/or with functional groups such as hydroxyl, thiol and/or amine groups. It should be noted that "dimethicone" (INCI name) corresponds to a poly(dimethylsiloxane) (chemical name), which is particularly preferred in some instances.

The non-volatile non-phenyl silicone oil is, in some embodiments, chosen from non-volatile dimethicone oils. In particular, these oils can be chosen from the following non-volatile oils:

polydimethylsiloxanes (PDMSs);

PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference ABIL WAX 9801 from Evonik Goldschmidt;

PDMSs comprising aliphatic groups, or functional groups such as hydroxyl, thiol and/or amine groups;

polyalkylmethylsiloxanes substituted with functional groups such as hydroxyl, thiol and/or amine groups; and polysiloxanes modified with fatty acids, fatty alcohols or polyoxyalkylenes, or mixtures thereof.

In some embodiments, non-volatile, non-phenyl silicone oils are chosen from polydimethylsiloxanes, alkyl dimethicones, and also PDMSs comprising aliphatic groups, in particular $C_2$-$C_{24}$ alkyl groups, and/or functional groups such as hydroxyl, thiol, and/or amine groups.

The non-phenyl silicone oil may be chosen in particular from silicones of the following formula:

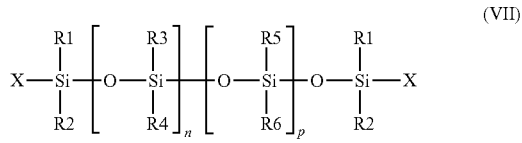

(VII)

wherein:

$R_1$, $R_2$, $R_5$, and $R_6$, which may be identical or different, are independently chosen from alkyl radicals containing 1 to 6 carbon atoms, $R_3$ and $R_4$, which may be identical or different, are independently chosen from alkyl radicals containing from 1 to 6 carbon atoms, a vinyl radical, an amine radical, or a hydroxyl radical, X is an alkyl radical containing from 1 to 6 carbon atoms, a hydroxyl radical, or an amine radical, and n and p are integers chosen so as to have a fluid compound, in particular of which the viscosity at 25° C. is between 9 centistokes (cSt) and 800 000 (cSt).

As non-volatile, non-phenyl silicone oils which can be used according to the invention, mention may be made of those for which:

the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil D M 60 000 by the company Wacker, the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning, the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

Additional Ingredients

In accordance with the disclosure, the hair care composition may include in the various embodiments at least one additional miscellaneous ingredient or additives such as other conditioning agents, cationic agents, humectants, preservatives, chelating agents, UV filters, pH adjusters, fragrance, pigments, colorants, anti-dandruff, seborrheic agents and other skin actives.

In some particular embodiments, the composition may include one or more components comprising potassium hydroxide; sodium hydroxide; acetamide mea; lactic acid; taurine; citric acid; gluconolactone; fragrance; one or more preservatives comprising chlorhexidine dihydrochloride, phenoxyethanol, benzoic acid; and combinations of these.

In accordance with the various embodiments, when present, an additive is from about 0.1% to about 10%, or from about 0.1% to about 8%, or from about 0.2% to about 7%, or from about 1% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

In accordance with the various embodiments, when present, the total amount of additive present in the compositions can range from about 0.1% to about 15%, or from about 0.5% to about 12%, or from about 1% to about 10%, or from about 1.5% to about 5% or any suitable combination, sub-combination, range, or sub-range thereof by weight, based on the weight of the composition. One of ordinary skill in the art, however, will appreciate that other ranges are within the scope of the invention.

Thus, when present, an additive is present, by weight, based on the total weight of the composition, from about 0.5, 0.6, 0.7, 0.8, 0.9, 1, 2, 3, 4, 5, 6, 7, 8, 9, 10, 11, 12, 13, 14, 15, 16, 17, 18, 19, to about 20 weight percent, including increments and ranges therein and there between.

In some particular embodiments, the composition includes one or more preservatives. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, benzoic acid, chlorhexidine digluconate, ethylenediamine-tetraacetic acid (EDTA), potassium sorbate, and/or grapefruit seed extract, or a mixture thereof. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, Vitamin E (tocopherol), and a mixture thereof. In some cases, the hair care compositions may include one or more preservatives selected from the group consisting of sodium benzoate, benzoic acid, chlorhexidine digluconate, chlorhexidine dihydrochloride, salicylic acid, phenoxyethanol, methyl paraben, and a mixture thereof.

In accordance with the various embodiments, when present, an additive in the form of one or more preservative is from about 0.1% to about 5%, or from about 0.2% to about 5%, or from about 1.5% to about 3% or any suitable combination, sub-combination, range, or sub-range thereof by weight, based on the weight of the composition. One of ordinary skill in the art, however, will appreciate that other ranges are within the scope of the invention.

Compositions, Methods of Use and Application, and Kits

The compositions described throughout the instant disclosure may be in a variety of different forms, including but not limited to gels, lotions, creams, emulsions, pastes, milks, sprays, serums, and the like. The compositions may be rinse-off or leave-in treatments.

In various embodiments, the composition is in the form of an aqueous solution. In an embodiment, the composition is in the form of an emulsion, such as an oil-in-water (O/W) emulsion. In one embodiment, the composition is a conditioner in the form of an O/W emulsion. In an embodiment, the compositions may be in the form of a dispersion. In an embodiment, the composition is a rinse-off treatment for conditioning and/or styling and/or shaping hair.

Additionally, when used on hair, the compositions may provide one or more desirable cosmetic and/or styling benefits to the hair, for example, smoothness, detangling, and shine. Accordingly, the compositions are useful in methods for conditioning hair, and methods for imparting frizz control, manageability, smoothness, detangling, and/or shine to hair. Accordingly, the instant disclosure encompasses methods for treating hair with the compositions of the instant disclosure. Such methods may include simply applying a composition of the instant disclosure to the hair, and optionally rinsing the hair.

In some cases, methods of using the compositions include shampooing and/or conditioning the hair with a composition of the instant disclosure. Such methods typically include applying an effective amount of a hair treatment composition of the instant disclosure to the hair, allowing the composition to remain on the hair for a period of time, and subsequently optionally rinsing the composition from the hair. The period of time for which the composition is allowed to remain on the hair is usually not long, e.g., not longer than about 5 minutes. Usually, the composition is merely allowed to remain on the hair for a period of time sufficient to incorporate the composition throughout the hair, for example, by lathering or spreading the composition throughout the hair using one's hands. The amount of time is sufficient for the composition to interact with the hair and any dirt, oil, contamination, etc., that may exist on the hair so that when rinsed, the agents of the composition can interact with the hair to condition it and confer styling benefits. Thus, the composition may be allowed to remain on the hair for about 5 seconds to about 30 minutes, about 5 seconds to about 15 minutes, about 5 seconds to about 10 minutes, about 5 seconds to about 5 minutes, about 10 seconds to about 5 minutes, or about 10 seconds to about 3 minutes.

As is common when using shampoo and/or conditioner and/or masque compositions, the hair may be wetted or rinsed with water prior to application of the hair treatment composition of the instant disclosure. Having water already in the hair can be helpful, e.g. for creating lather when applying compositions such as shampoos because the water interacts with the surfactants of the shampoo's surfactant system.

Typically, a shampoo and a conditioner are used in a hair care routine in the form of a bundle system in order to cleanse then condition the hair. Optionally, another composition, e.g. a masque, may be used after a conditioner in order to impart deeper conditioning to the hair or to deliver other active or benefit agents such as styling agent to the hair. Optionally, a pre-shampoo treatment composition may also be applied onto hair before shampooing in order to deliver additional benefits to the hair. Optionally, an in-shower treatment composition may be mixed, in situ on hair or before treating hair, with a shampoo and/or conditioner in order to enhance the cleansing and/or conditioning of the hair. As such, it is possible to have kits comprising one, two, three, or more of these compositions, each composition packaged separately. Any known means of packaging the compositions separately in a kit may be used, e.g. separate bottles or containers for each composition, a single bottle with separate compartments for each composition, etc.

Implementation of the present disclosure is provided by way of the following Examples. The Examples serve to illustrate the technology, without being limiting in nature.

EXAMPLES

The following Examples are intended to be non-restrictive and explanatory only. The ingredient amounts in the compositions/formulas described below are expressed in % by weight, based on the total weight of the composition.

Several formulas were produced, in some specific examples having ingredients that include those listed in the tables below. Not all components of the compositions are listed in the representative components Table 2, below. Table 2 lists raw materials, and the subsequent tables list amounts of actives, with the understanding that not all actives are present at 100% in the raw materials. The balance of all formulas was water.

Example I: Key Raw Materials

Various components as described and exemplified herein may be provided as a raw material blend containing solvents and surfactants.

TABLE 2

Representative Components

| Component | Ingredient | Trade Name, Supplier and Concentration |
|---|---|---|
| Polysaccharide | Inulin | Supplied by Creachem |
| Wax: a silicone-free wax derived from the Wild *Euphorbia Cerifera* plant | candelilla wax | Light Special candelilla Real; Supplied by Multiceras |
| Cationic surfactant | Behentrimonium Chloride | Supplied by Clariant |
| Film-forming aminosilicone polymer | PolySilicone-29 | Supplied by Momentive |

Example 2: Inventive Compositions

TABLE 3

| | Inventive Compositions 1-6 | | | | | |
|---|---|---|---|---|---|---|
| INGREDIENT INCI US | INV 1 | INV 2 | INV 3 | INV 4 | INV 5 | INV 6 |
| BEHENTRIMONIUM CHLORIDE | 2.9625 | 2.9625 | 2.9625 | 0.948 | 2.923 | 4.9375 |
| NONIONIC SURFACTANTS: TRIDECETH-10 AND/OR TRIDECETH-6 AN/OR TRIDECETH-6 AND/OR STEARETH-6 AND/OR | 0.6 | | 0.3 | | 0.4 | 0.904 |

TABLE 3-continued

Inventive Compositions 1-6

| INGREDIENT INCI US | INV 1 | INV 2 | INV 3 | INV 4 | INV 5 | INV 6 |
|---|---|---|---|---|---|---|
| COCETH-7 AND/OR PPG-1 TRIDECETH-6 | | | | | | |
| CETYL ESTERS | 1.5 | | | 0.4 | 0.5 | 1.5 |
| POLYSILICONE-29 | 0.15 | 0.15 | 0.15 | 0.15 | 0.15 | 0.3 |
| C15-19 ALKANE | | | | | | 1 |
| ACRYLAMIDOPROPYLTRIMONIUM CHLORIDE/ACRYLATES COPOLYMER | | | | | | 0.43 |
| CETRIMONIUM CHLORIDE | | | | | 0.03 | |
| SORBITAN OLEATE | 0.04 | | | | 0.04 | |
| ACETAMIDE MEA | | | | | | 1.4 |
| LAURYL PEG/PPG-18/18 METHICONE | | | | 0.375 | | |
| POLYQUATERNIUM-46 | 1 | 0.568 | | | | |
| VP/VA COPOLYMER | | | | 0.5 | | |
| POLYQUATERNIUM-6 | | 0.08 | 0.08 | | 0.12 | 0.268 |
| POLYQUATERNIUM-37 | 1 | | | | 1 | |
| ISOSTEARYL ALCOHOL | | | | 0.125 | | |
| VP/DIMETHYLAMINOETHYL METHACRYLATE COPOLYMER | | 0.5955 | | | | |
| HYDROXYPROPYL GUAR | 0.15 | | | | | 0.4 |
| PROPYLENE GLYCOL DICAPRYLATE/DICAPRATE | 0.7 | | | | 0.7 | |
| HYDROXYPROPYL GUAR HYDROXYPROPYLTRIMONIUM CHLORIDE | | | | | 0.5 | |
| SORBITAN ISOSTEARATE | | | | | | 0.02 |
| *EUPHORBIA CERIFERA* (CANDELILLA) WAX | 2.5 | 1.5 | 3 | 3 | 0.5 | 1 |
| PEG-100 STEARATE | 0.075 | | 0.06 | | | |
| INULIN | 0.97 | 0.97 | 0.97 | 0.97 | 1.455 | 0.97 |
| GLUCONOLACTONE | 0.5 | | 0.5 | | | |
| AMINOPROPYL TRIETHOXYSILANE | | | | | 1 | |
| POTATO STARCH MODIFIED | | | | 0.86 | | |
| DIMETHICONOL | | 0.96 | | | | |
| DIMETHICONE | 2 | 7.04 | 1.6 | | | |
| AMODIMETHICONE | 0.5 | | 0.4 | | 1.71 | |
| CETEARYL ALCOHOL | 7 | 7 | 7 | 2 | 7.6 | 7 |
| PLANT OILS AND BUTTERS | | 4.5 | | | 3.0 | |
| ORGANIC SOLVENTS: ISOPROPYL ALCOHOL AND/OR GLYCERIN OR DIPROPYLENE GLYCOL AND/OR PROPANEDIOL | <10.0 | <10.0 | <10.0 | <10.0 | <10.0 | <10.0 |
| ADDITIVES: PRESERVATIVES, VITAMINS, PH ADJUSTER, NEUITRALIZERS, COLORANTS, AMINO ACIDS | <5.0 | <5.0 | <5.0 | <5.0 | <5.0 | <5.0 |
| WATER | Q.S.100 | Q.S.100 | Q.S.100 | Q.S.100 | Q.S.100 | Q.S.100 |

Example 3: Comparative Composition

TABLE 4

Commercial Shampoo

| INGREDIENT INCI US | COMP SHAMPOO |
|---|---|
| AMODIMETHICONE | 0.6 |
| LAURETH-5 CARBOXYLIC ACID | 0.72 |
| HEXYLENE GLYCOL | 0.5 |
| POLYQUATERNIUM-7 | 0.495 |
| SODIUM LAURETH SULFATE | 8.05 |
| PROPYLENE GLYCOL | 0.24 |
| PEG-60 HYDROGENATED CASTOR OIL | 0.15 |
| COCAMIDE MIPA | 0.7 |
| COCO-BETAINE | 4.5 |
| WATER | Q.S. 100 |
| PEG-55 PROPYLENE GLYCOL OLEATE | 0.24 |
| PLANT EXTRACTS AND PLANT OILS | <0.5 |
| ADDITIVES: PRESERVATIVES, VITAMINS, PH ADJUSTER, NEUTRALIZERS, COLORANTS, SODIUM CHLORIDE | <5.0 |

TABLE 5

COMMERCIAL CONDITIONER

| INGREDIENT INCI US | COMP CONDITIONER |
|---|---|
| TRIDECETH-6 | 0.15 |
| CETRIMONIUM CHLORIDE | 0.03 |
| ISOPROPYL ALCOHOL | 0.576 |
| CETEARYL ALCOHOL | 6.5 |
| AMODIMETHICONE | 1.71 |
| WATER | Q.S. 100 |

TABLE 5-continued

COMMERCIAL CONDITIONER

| INGREDIENT INCI US | COMP CONDITIONER |
|---|---|
| PLANT EXTRACTS AND PLANT OILS | <0.5 |
| ADDITIVES: PRESERVATIVES, VITAMINS, PH ADJUSTER, NEUTRALIZERS, COLORANTS | <5.0 |

Example 4: Expert Testing

A cohort of 10 subjects, each having medium to long hair, with average to course hair texture, and a curl pattern of I-III* were recruited into a study. Each subject's hair was treated with Comparative Shampoo on the full head of hair; thereafter, half of the head of hair for each subject was treated with Comparative Conditioner, and half of the head of hair for each subject received Inventive Conditioner 3, which is a composition according to the disclosure that includes a blend of polyquaternium cationic polymers together in a cationic system with a novel association of polysaccharide, for example, Inulin, a wax, for example, candelilla Wax, a cationic surfactant, for example, Behentrimonium Chloride, and a film-forming polymer, for example polysilicone-29, and including fatty compounds, silicone and styling polymer. After rinsing to remove the applied conditioner to the test half of each subject's hair, the hair was blow-dried to style.

Referring now to Table 6, below, the expert evaluator reported on the performance of the control and test subject hair with respect to factors that include convenience, care, shape and style, and usage.

TABLE 6

| PERFORMANCE FACTOR | PERFORMANCE FEATURE | EXPERT GRADE (INV vs COMP) |
|---|---|---|
| Convenience | Easy combing | ≥ |
|  | Easy Blow-dry | ≥ |
|  | Fast Blow-dry | > |
| Care | Smooth Feel Rinsing | < |
|  | Smooth Visual after 24 hours | ≥ |
|  | Shine | ≥ |
| Shape & Style | Discipline after styling | ≥ |
|  | Discipline 24 hours after styling | ≥ |
|  | Shape Control 24 hours after styling | ≥ |
| Usage | Product Texture & Aspects | < |
|  | Product Clean Feel | ≥ |

Example 5: Consumer Testing

A cohort of 14 subjects, age 16-65, each having medium to long hair, with average to course hair texture, and a curl pattern of I-III* were recruited into a study. Each subject used comparative shampoo and Inventive Composition 3 at least three times per week in place of the subject's usual conditioner and then styled hair, with or without usual styling products.

Test subjects reported that the performance of the Inventive compositions was comparable to their usual products in terms of regimen, and experience with respect to stylability and smoothness of hair after product use and the product was easy to rinse, though somewhat difficult to immediately spread. The hair was not weighed down (light), did not get greasy.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−1%, 2%, 3%, 4%, or 5% of the indicated number.

Some of the various categories of components identified for the hair care compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

All numbers herein are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention. Similarly, the compositions may include less than 0.5 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair care composition, comprising:
   at least one polysaccharide;
   at least one wax;
   at least one cationic surfactant;
   at least one film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane;
   water; and
   optionally, at least one fatty compound other than fatty alcohols,
   wherein the hair care composition is free of salts other than amine salts, ammonium salts, diammonium salts, triammonium salts, alkanolammonium salts, alkali metal salts, and alkaline earth metal salts, and
   wherein the hair care composition is free of salts other than salts of the at least one polysaccharide, salts of the at least one cationic surfactant, and, optionally, salts of the at least one fatty compound other than fatty alcohols.

2. The hair care composition according to claim 1, wherein the at least one polysaccharide is a plant gum selected from the group consisting of inulin, carrageenan, pullulan, and combinations thereof.

3. The hair care composition according to claim 1, wherein the at least one polysaccharide is present in an amount from about 0.2% to about 10% by weight of the composition.

4. The hair care composition according to claim 1, wherein the at least one wax is selected from the group consisting of candelilla wax, microcrystalline wax, beeswax, and combinations thereof.

5. The hair care composition according to claim 1, wherein the at least one wax is present in an amount from about 0.1% to about 10% by weight of the composition.

6. The hair care composition according to claim 1, wherein the at least one cationic surfactant is selected from the group consisting of behentrimonium chloride, cetrimonium chloride, cetrimonium methosulfate, stearimonium chloride, behentrimonium methosulfate, distearyldimonium chloride, dicetyldimonium chloride, methosulfate, oleamidopropyl dimethylamine, linoleamidopropyl dimethylamine, stearamidopropyldimethylamine, brassicamidopropyldimethylamine, and combinations thereof.

7. The hair care composition according to claim 1, wherein the at least one cationic surfactant is present in an amount from about 0.5% to about 10% by weight of the composition.

8. The hair care composition according to claim 1, wherein the at least one film-forming aminosilicone polymer is polysilicone-29.

9. The hair care composition according to claim 1, wherein the at least one film-forming aminosilicone polymer is present in an amount from about 0.5% to about 20% by weight of the composition.

10. The hair care composition according to claim 1, comprising at least one fatty alcohol selected from the group consisting of cetearyl alcohol, cetyl alcohol, stearyl alcohol, behenyl alcohol, lauryl alcohol, and combinations thereof.

11. The hair care composition according to claim 1, further comprising at least one additional ingredient selected from the group consisting of the at least one fatty compound other than fatty alcohols, at least one cationic polymer, at least one nonionic polymer, at least one styling polymer, at least one silicone compound, and combinations thereof.

12. The hair care composition according to claim 11, wherein, when present:
    the at least one fatty compound is selected from the group consisting of *Ricinus communis* (castor) seed oil, butyrospermum parkii (shea) butter, cetyl esters, C15-19 alkane, *Elaeis guineensis* (palm) oil, and combinations thereof;
    the at least one cationic polymer is selected from the group consisting of polyquaternium-6, polyquaternium-46, polyquaternium-37, hydroxypropyl guar hydroxypropyltrimonium chloride, and combinations thereof;
    the at least one nonionic polymer comprises hydroxypropyl guar, potato starch modified, or a combination thereof;
    the at least one styling polymer is selected from the group consisting of vp/va copolymer, vp/dimethylaminoethylmethacrylate copolymer, acrylamidopropyltrimonium chloride/acrylates copolymer, or combinations thereof; and
    the at least one silicone compound is selected from the group consisting of lauryl PEG/PPG-18/18 methicone, dimethicone, dimethiconol, amodimethicone aminopropyl triethoxysilane, and combinations thereof.

13. The hair care composition according to claim 12, wherein, when present:
    each of the at least one fatty compound other than fatty alcohols is present from about 0.1% to about 10% by weight of the composition;
    each one of the at least one cationic polymer, at least one nonionic polymer, at least one styling polymer, or combinations thereof is present from about 0.1% to about 10% by weight of the composition; and
    each of the at least one silicone compound is present in an amount from about 0.1% to about 10%, by weight of the composition.

14. The hair care composition according to claim 1, further comprising a cosmetically acceptable carrier comprising the water which is present in an amount that is at least 20% by weight of the composition.

15. The hair care composition according to claim 14, further comprising in the cosmetically acceptable carrier at least one water-soluble solvent comprising polyols.

16. A hair care composition, comprising:
    at least one polysaccharide comprising at least one plant gum;
    at least one wax comprising candelilla wax;
    at least one cationic surfactant;
    at least one film-forming aminosilicone polymer comprising polysilicone-29;
    at least one polymer selected from the group consisting of cationic polymers, nonionic polymers, styling polymers and combinations thereof;
    at least one fatty alcohol;
    at least one fatty compound other than fatty alcohols; and water
    wherein the hair care composition is free of salts other than amine salts, ammonium salts, diammonium salts, triammonium salts, alkali metal salts, alkanolammonium salts, and alkaline earth metal salts, and
    wherein the hair care composition is free of salts other than salts of the at least one polysaccharide, salts of the at least one cationic surfactant, and salts of the at least one fatty compound other than fatty alcohols.

17. The hair care composition according to claim 16, wherein:
    the at least one plant gum of the at least one polysaccharide is selected from the group consisting of inulin, carrageenan, pullulan, and combinations thereof;
    the at least on one cationic surfactant comprises behentrimonium chloride;
    the at least one fatty compound other than fatty alcohols comprises *Ricinus communis* (castor) seed oil, butyrospermum parkii (shea) butter, cetyl esters, C15-19 alkane, *Elaeis guineensis* (palm) oil, or combinations thereof;
    the at least one polysaccharide is present in an amount from about 0.2% to about 10%, by weight of the composition;
    the at least one wax is present in an amount from about 0.1% to about 5%, by weight of the composition;
    the at least on one cationic surfactant is present in an amount from about 0.5% to about 10%, by weight of the composition;
    the at least one film-forming aminosilicone polymer is present in an amount from about 0.5% to about 20%, by weight of the composition; and
    the at least one fatty compound other than fatty alcohols is present from about 0.1% to about 10%, by weight of the composition.

18. The hair care composition according to claim 16, wherein the at least one polymer comprises:
    the cationic polymers selected from the group consisting of polyquaternium-6, polyquaternium-46, polyquaternium-37, hydroxypropyl guar hydroxypropyltrimonium chloride, and combinations thereof, wherein each of the cationic polymers, if present, is present from about 0.1% to about 10% by weight of the composition;
    the nonionic polymers selected from the group consisting of hydroxypropyl guar, potato starch modified, and combinations thereof;
    the styling polymers selected from the group consisting of, vp/va copolymer, vp/dimethylaminoethylmethacrylate copolymer, acrylamidopropyltrimonium chloride/acrylates copolymer, and combinations thereof, wherein each of the styling polymers, if present, is present from about 0.1% to about 10% by weight of the composition; or
    combinations thereof.

19. The hair care composition according to claim 16, further comprising at least one silicone compound selected from the group consisting of lauryl PEG/PPG-18/18 methicone, dimethicone, dimethiconol, amodimethicone aminopropyl triethoxysilane, and combinations thereof, wherein each of the at least one silicone compound is present in an amount from about 0.1% to about 8%, by weight of the composition.

20. The hair care composition according to claim 16, further comprising at least one component selected from the group consisting of potassium hydroxide, sodium hydroxide acetamide mea, lactic acid, taurine, citric acid, gluconolactone, fragrance, at least one preservative comprising at least one of chlorhexidine dihydrochloride, phenoxyethanol, benzoic acid, or combinations thereof, and combinations thereof.

21. A hair care composition, comprising:
at least one polysaccharide comprising inulin and, optionally, carrageenan, pullulan, or combinations thereof;
at least one wax comprising candelilla wax;
at least one cationic surfactant comprising behentrimonium chloride;
at least one film-forming aminosilicone polymer comprising polysilicone-29; and
water present in an amount that is at least 20% by weight of the composition.

22. A method of styling hair, comprising:
1) treating hair with a shampoo composition;
2) rinsing the hair with water;
3) treating the hair with a composition comprising:
   at least one polysaccharide;
   at least one wax;
   at least one cationic surfactant;
   at least one film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane; and
   water;
4) optionally, treating the hair with a conditioner composition; and
5) rinsing the hair with water,
   wherein the hair care composition is free of salts other than amine salts, ammonium salts, diammonium salts, triammonium salts, alkanolammonium salts, alkali metal salts, and alkaline earth metal salts, and
   wherein the hair care composition is free of salts other than salts of the at least one polysaccharide, salts of the at least one cationic surfactant, and, optionally, salts of the at least one fatty compound other than fatty alcohols.

* * * * *